United States Patent [19]
Schubert et al.

[11] 4,114,464
[45] Sep. 19, 1978

[54] ARTIFICIAL HAND AND DRIVE APPARATUS FOR SUCH HAND

[75] Inventors: Klaus-Peter Schubert, Feldkirchen; Hartmut Keller, Weyarn; Jürgen J. Hildebrandt, Brunnthal, all of Fed. Rep. of Germany

[73] Assignee: Messerschmitt-Bolkow-Blohm Gesellschaft mit beschrankter Haftung, Munich, Fed. Rep. of Germany

[21] Appl. No.: 767,678

[22] Filed: Feb. 11, 1977

[30] Foreign Application Priority Data
Feb. 25, 1976 [DE] Fed. Rep. of Germany ....... 2607499

[51] Int. Cl.² ............................................. F16H 27/02
[52] U.S. Cl. ..................................... 74/89.14; 3/12.7
[58] Field of Search .................. 74/89.14, 425; 3/12.7

[56] References Cited
U.S. PATENT DOCUMENTS

| | | | |
|---|---|---|---|
| 2,903,896 | 9/1959 | Greene | 74/89.21 |
| 3,012,448 | 12/1961 | Abraham | 74/89.14 |
| 3,683,423 | 8/1972 | Crapanzano | 3/12.7 |
| 3,822,418 | 7/1974 | Yakobson et al. | 3/12.7 |
| 3,901,547 | 8/1975 | Skinner | 3/12.7 |

Primary Examiner—Benjamin W. Wyche
Assistant Examiner—Wesley S. Ratliff, Jr.
Attorney, Agent, or Firm—W. G. Fasse; W. W. Roberts

[57] ABSTRACT

An artificial hand having at least one finger and a thumb is provided with a drive motor and a gear to open and close the finger and thumb. A gear wheel is secured to each joint where the finger and thumb is connected to the hand proper. A motor driven worm gear meshes with both gear wheels and reversible gears are interposed between the motor and the worm gear, whereby an axially displaceable shaft maintains the interconnection between the drive means and the worm gear.

9 Claims, 3 Drawing Figures

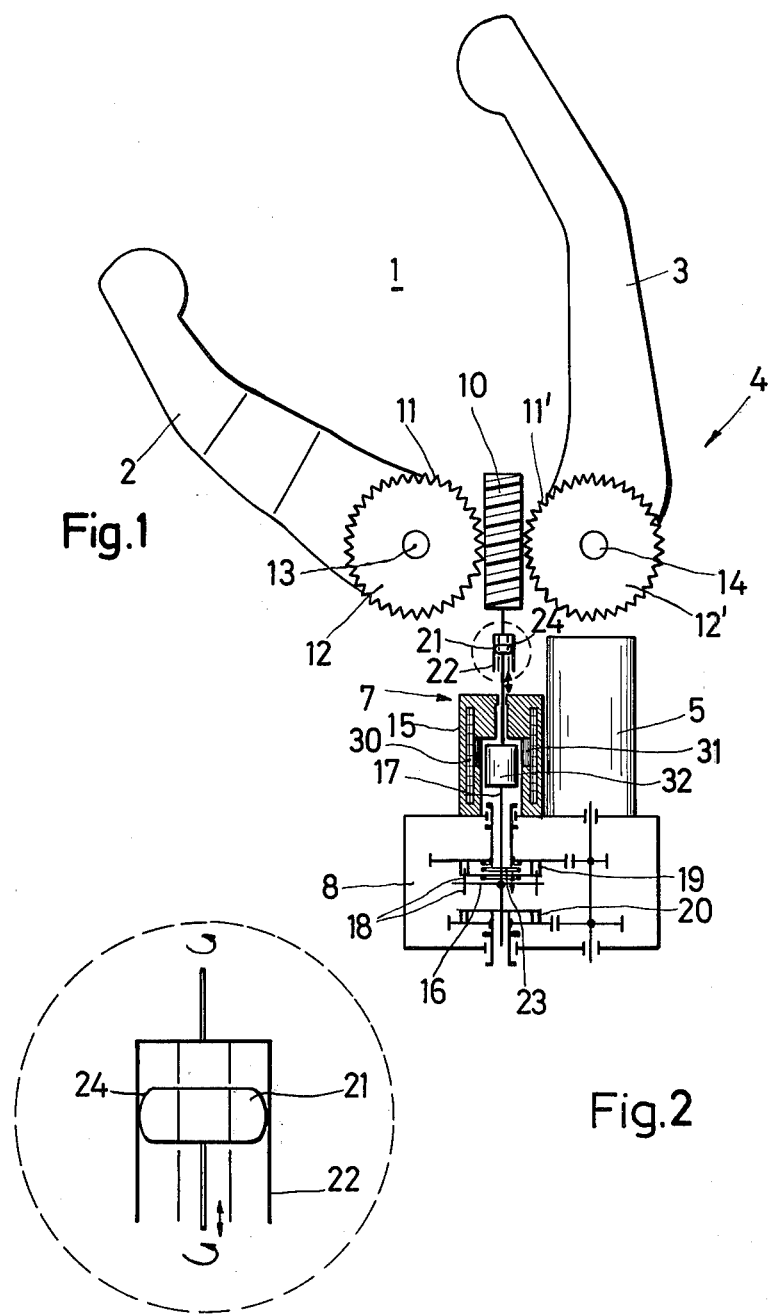

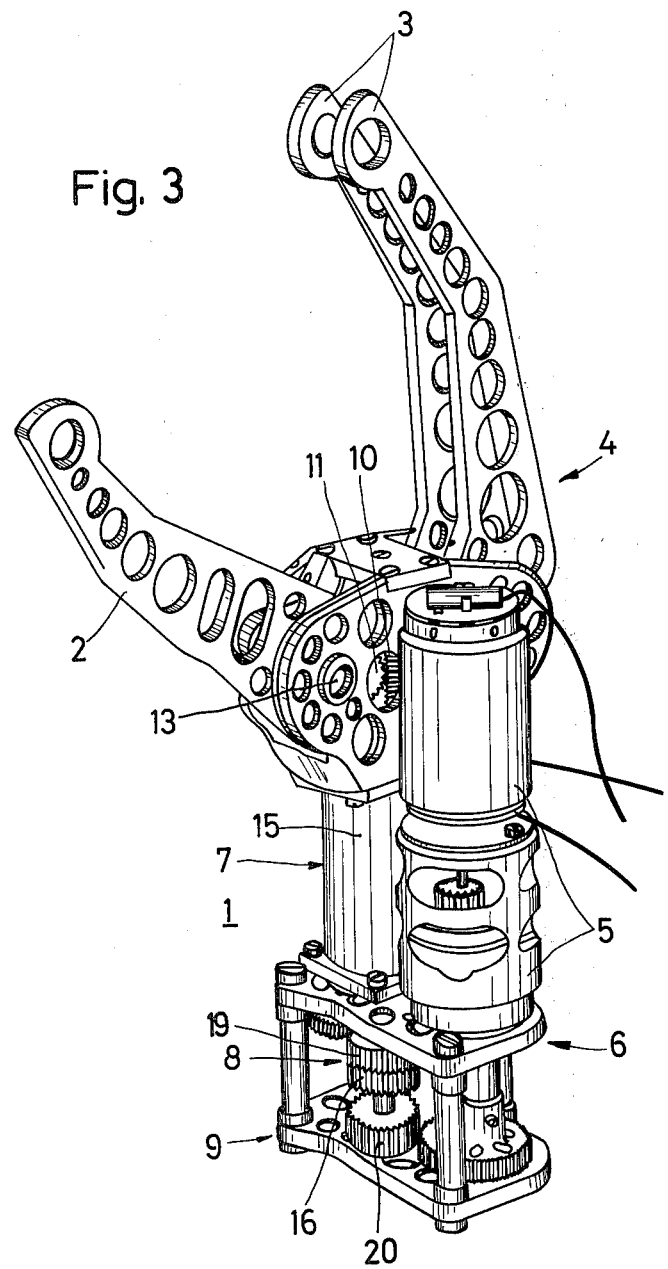

ARTIFICIAL HAND AND DRIVE APPARATUS FOR SUCH HAND

BACKGROUND OF THE INVENTION

The invention relates to an artificial hand and to a drive apparatus for such a hand, especially for the fingers of the hand, including a movable thumb and at least one further finger movable in a direction opposite the direction of a thumb movement.

Artificial hands and arm prosthesis with mechanically movable fingers are intended to enable the user thereof to perform the many gripping functions as they occur in day to day use, whereby the time required to perform each function should be minimized. Further, any artificial limb should approximate the appearance of a natural limb as much as possible.

In order to minimize the operational time of artificial limbs, it is necessary to provide drive means for the movable elements such as the finger and the thumb, which are adaptable in a wide range to the continuously varying requirements, especially with regard to the gripping force applied by the drive means to the fingers. Further, the drive means must be lockable in the gripping position of the fingers.

Efforts to meet the foregoing requirements have been made heretofore. Thus, pneumatic drive systems are known which receive their driving energy from high pressure bottles or air pressure conduits. Even gas pressure cartridges have been used as the energy supply for artificial limbs. German Patent Publication (DOS) No. 2,433,710 illustrates a device employing high pressure bottles which are rechargeable. However, all of these devices require an energy supply, the replenishing of which is time consuming for the invalid or user and the replenishing can take place only at specific locations. As a result, the range of use of prior art devices is substantially limited.

Other known drive mechanisms, for example, such as are described in German Patent Publication (DOS) No. 2,426,711, use an electric motor connected to the drive means for operating the fingers by means of rope and pulley arrangements. This type of drive requires additional locking mechanisms for arresting the fingers in the gripping position. A disadvantage common to the just described drive mechanisms with rope and pulleys as well as to drive mechanisms employing a pneumatic source of energy is seen in that these devices are of a relatively complicated structure and hence, are trouble prone, whereby the use value of these devices is substantially diminished.

OBJECTS OF THE INVENTION

In view of the above, it is the aim of the invention to achieve the following objects, singly or in combination:

to provide a drive mechanism for an artificial hand which is free of the disadvantages of the prior art and which will provide a reliable operation while simultaneously requiring a relatively inexpensive and simple structure;

to provide an artificial hand which, due to the type and coordination of its elements, its very versatile in its use and which fulfills the above stated requirements;

to use gear wheels in the drive of the fingers of an artificial hand so that an inherent locking of the gripping position will be accomplished; and to incorporate in the gear drive means different gears so that the user may have a choice of selecting a fast or slower operation of the fingers, and of the gripping force.

SUMMARY OF THE INVENTION

According to the invention there is provided a drive means for an artificial hand in which gear wheels are secured to the thumb, and the finger at the point where the finger and thumb merge into the hand proper, whereby the pivot or journal axis of the thumb and finger coincides with the rotational axis of the gear wheels. A worm gear is arranged to mesh with both gear wheels, whereby the worm gear is movable up and down and driven by a motor through reversible gear means.

According to one embodiment of the invention, a relatively simple, short circuit proof electric gear drive motor is employed which cooperates with a simple two or multi-stage reversible gear drive operable by means of an electromagnetic shift or clutch mechanism.

The arrangement of the elements relative to each other results in a structure which can be incorporated in a prosthetic limb largely resembling the natural shape of the respective limb. This is especially possible because the drive shaft of the reversible drive gear and the magnetic clutch are arranged centrally of the hand proper, whereby the rotational axis of the worm gear and the rotational axis of the drive shaft are longitudinally aligned with each other, whereas the electric motor with its adaptor gear is arranged along side one edge of the hand proper and the motor axis extends in parallel to the first mentioned two axes.

The just mentioned reversible gear drive means comprises suitably a clutch disc which is secured to an axially displaceable shaft which in turn is shiftable against the force of a resetting spring by means of a lifting magnet in the axial direction. The drive output end of the shaft is provided with means for engaging the worm gear continuously, even when the latter is laterally displaced. For example, a hexagonal end of the drive shaft may slidingly fit into a hexagonal opening or end member of the worm gear. The clutch disc is preferably provided on each side with a crown gear capable of alternately engaging respective gear wheels of the gear drive. When the clutch is released by the lift magnet, the spring bias assures that the crown gear preferably meshes with the fast drive of the fingers.

The above mentioned hexagonal end of the drive shaft is preferably provided with curved side surfaces to improve the slidability of the shaft and then the female end of the worm gear.

BRIEF FIGURE DESCRIPTION

In order that the invention may be clearly understood, it will now be described, by way of example, with reference to the accompanying drawings, wherein:

FIG. 1 is a somewhat simplified side view of a drive mechanism for the fingers of an artificial hand, according to the invention;

FIG. 2 illustrates on an enlarged scale, the male and female coupling means between the drive shaft and the worm gear; and FIG. 3 illustrates the correlation of the structural elements of the hand, including the drive means, whereby the external covering such as a glove has been removed.

DETAILED DESCRIPTION OF PREFERRED EXAMPLE EMBODIMENTS

The drive mechanism 1, for an artificial hand shown schematically in FIG. 1 has a thumb 2 and one or several fingers 3 to form an artificial hand 4. A drive motor 5 is supported on a frame structure shown in FIG. 2. Preferably, the drive motor is an electrical motor of the short circuit proof type and includes in its housing an adaptor gear. The motor 5 is arranged in the area of the hand proper alongside the outer hand edge 6, or rather, between the outer hand edge 6 and the thumb 2. The middle area of the hand is referred to as the hand proper 7.

The gear drive motor 5 drives a reversible gear 8 arranged in the frame structure 9 near the root or wrist of the hand not shown. The rotational axis of the motor 5 and of the respective gears extends in parallel to the drive shaft 17 which in turn is axially aligned with the rotational axis of a worm gear 10. A first gear wheel 12 meshes with its gear teeth 11 with the worm gear 10. The first gear wheel 12 is rigidly secured to the thumb 2 so that the journal axis 13 and the rotational axis of the gear wheel 12 coincide. A second gear wheel 12' meshes with its gear teeth 11' with the worm gear 10 and is rigidly secured to the finger 3 so that the journal axis 14 of the finger 3 coincides with the rotational axis of the second gear wheel 12'.

The drive means so far described have an inherent locking feature which enables the stopping and holding of the thumb and fingers in any position, whereby these fingers and thumb may be opened and closed conveniently and quickly.

The gripping force is determined by the short circuit torque of the electric motor 5 and by the gear reduction of the respective gear drive means. The gripping speed, or rather, the speed of the movement of the thumb and finger is determined by the r.p.m. of the motor 5 and the respective gear reduction.

The gripping force and the movement speed of the thumb and finger may be changed by means of an electro-magnet 15 which shifts a clutch disc 16 secured to an axially displaceable drive shaft 17. The clutch disc 16 is provided on each of its sides with laterally extending crown gears 18 arranged for alternate meshing with gears 19 and 20, such as ring gears of the reversible gear drive 8.

In operation, when the energizing coil 30 of the lift magnet 15 is not energized, the crown gear 18 of the clutch disc 16 meshes with the ring gear 20 of the reversible gear 8. Such meshing results in a relatively fast motion of the thumb 2 and the finger 3, whereby the gripping force may be limited, for example, within a range of 1 to 2kg. When it is desired to increase the gripping force after a rapid and careful gripping action, the owner could switch over, to the higher gripping force by energizing the coil 30 of the lifting magnet 15 to develop a holding force, for example, within a range of 8 to 10kg. This operation is illustrated in FIGS. 1 and 3 showing the armature 32 of the magnet 15 in the energized position, whereby the gear 19 meshes with the upwardly facing crown gear 18 of the clutch plate 16.

It is an advantage of the just described mechanism, according to the invention, that the fingers 2 and 3 are positively locked in any desired position by the worm gear 10 meshing with the gear wheels 12 and 12'. Thus, additional arresting or locking means as well as means for releasing the arresting means are obviated. The positive locking of the fingers in any desired position has the further advantage that the user is assured of a certain gripping action since the release of the gripping force is accomplished only by reversing the rotational direction of the drive motor 5. Such reversal of the motor 5 may simply be accomplished by reversing its drive voltage while simultaneously switching off the energization of the lifting magnet 15. This feature has the further advantage that opening of the hand is accomplished always with the desired high speed.

Referring to FIG. 2, the drive output end 21 of the drive shaft 17 is provided with a suitable, interlocking shape relative to a tubular end 22 forming part of the worm gear 10. A hexagonal shape has been found to be suitable for this purpose, whereby the sliding axially up and down of the output end 21 inside the female tubular member 22 is improved by providing the circumferential surface of the output end 21 with a curved shape 24. Thus, only a small fraction of the energy of the lifting electro-magnet 15 is required for the friction of the male element 21 in the female element 22, especially since the spring 23 which maintains the gears meshing in the rapid gear position when the magnet 15 is switched off, may be a rather soft spring.

In addition to the above mentioned advantages of the invention, it should also be noted that the control of the present motor and gear drive is accomplished with very simple means such as the well known, so-called "myo"-electric devices. The very low energy requirement of the present drive mechanism is another advantage because it makes possible to incorporate in the structure, a battery or rechargeable battery which normally provides sufficient energy for a whole days work under most circumstances.

Incidentally, the lift magnet 15 has an inner gap which may be filled with a non-magnetic material 31. If desired, such gap may also be omitted.

Due to the construction of the reversible shifting gear which includes crown gears with gear teeth edges, it is possible to accomplish a shifting in any finger position. All control functions may be accomplished without any time delays, for example, by means of the above mentioned "myo"-electric control means, whereby there is no need for switching operations to be performed, for example, by a sound limb of the user. Furthermore, the relative arrangement of the elements greatly facilitates the enveloping of the mechanical structure by glove means which provide a substantially natural appearance of the artificial limb.

Although the invention has been described with reference to specific example embodiments, it will be appreciated, that it intended to cover all modifications and equivalents within the scope of the appended claims.

What is claimed is:

1. An artificial hand comprising frame means constituting the hand proper, a thumb, first journal means operatively connecting the thumb to said frame means, finger means, second journal means operatively connecting said finger means to said frame means, first gear means secured to said thumb for rotating the thumb about the first journal means, second gear means secured to said finger means for rotating the finger means about said second journal means, said thumb and finger means being arranged opposite each other to form gripping tongues, worm gear means operatively interposed between said first and second gear means in such a position that both gear means mesh with said worm gear means simultaneously, motor means secured to said frame means, and reversible gear drive means supported by said frame means and operatively interposed between said worm gear means and said motor means for rotating said worm gear means, whereby said gripping tongues may be opened by the rotation of said worm gear means in one direction and closed by the rotation of said worm gear means in the opposite direction.

2. The hand of claim 1, wherein said motor means is shortcircuit proof, and wherein said reversible gear drive means comprise a plurality of gear steps, said hand further comprising shift means operatively connected to said reversible gear drive means for reversing the direction of rotation of said worm gear means.

3. The hand of claim 2, wherein said shift means comprise electromagnetic clutch means arranged in said hand proper, said reversible gear drive means having a drive shaft arranged in axial alignment with the axis of rotation of said worm gear means, said motor means comprising adapter gear means having an axis of rotation extending in parallel to said drive shaft of said reversible gear drive means and in parallel to the rotation axis of said worm gear means, said motor means also being arranged in said hand proper alongside one edge thereof.

4. The hand of claim 1, further comprising shift means including electro-magnetic clutch means having a clutch disc, shaft means, said clutch disc being secured to said shaft means, spring means biasing said shaft means, said electro-magnetic clutch means including a lift magnet means for moving said shaft means against the bias of said spring means axially relative to said worm gear means, means operatively supporting said shaft means for axial movement, and means operatively connecting said shaft means to said worm gear means in a force transmitting manner in all axial positions of said shaft means.

5. The hand of claim 4, wherein said clutch disc comprises crown gears on both sides, said reversible gear drive means comprising gear wheels arranged on both sides of said crown gears for alternately engaging said crown gears of said clutch disc.

6. The hand of claim 5, wherein said reversible gear drive means comprise different size gear wheels to provide different gear reduction ratios, said spring means engaging said clutch disc with the gear wheel providing the lower gear reduction ratio when said electro-magnetic clutch means is not energized.

7. The hand of claim 4, wherein said means operatively connecting said shaft means to said worm gear means comprise a female tubular element having a predetermined inner cross sectional shape and a male element having an outer shape fitting into said female tubular element for axial movement therein.

8. The hand of claim 7, wherein said male element forms a hexagonal end of said shaft means, and wherein said female tubular element forms one end of said worm gear means with a respective hexagonal inner cross sectional shape.

9. The hand of claim 8, wherein said hexagonal end of said shaft means has curved sides.

* * * * *